United States Patent
Wilson et al.

(10) Patent No.: US 6,908,613 B2
(45) Date of Patent: Jun. 21, 2005

(54) CHIMERIC HUMAN PAPILLOMAVIRUS (HPV) L1 MOLECULES AND USES THEREFOR

(75) Inventors: Susan D. Wilson, Silver Spring, MD (US); Wendy White, Germantown, MD (US); JoAnn Suzich, Washington Grove, MD (US); Brian Mullikin, Mt. Airy, MD (US)

(73) Assignee: MedImmune, Inc., Gaithersburg, MD (US)

(*) Notice: Subject to any disclaimer, the term of this patent is extended or adjusted under 35 U.S.C. 154(b) by 0 days.

(21) Appl. No.: 09/876,256

(22) Filed: Jun. 8, 2001

(65) Prior Publication Data

US 2004/0224305 A1 Nov. 11, 2004

Related U.S. Application Data

(60) Provisional application No. 60/212,839, filed on Jun. 21, 2000.

(51) Int. Cl.⁷ .............................................. A61K 39/00
(52) U.S. Cl. ................................ 424/192.1; 424/204.1; 435/69.1; 435/69.7; 530/300
(58) Field of Search .......................... 424/204.1, 192.1; 435/69.7, 69.1; 530/300

(56) References Cited

U.S. PATENT DOCUMENTS

| 5,618,536 A | 4/1997 | Lowy et al. |
| 5,855,891 A | 1/1999 | Lowy et al. |
| 6,066,324 A | 5/2000 | Gissmann et al. |

FOREIGN PATENT DOCUMENTS

| WO | WO 96/11272 | * | 4/1996 |
| WO | WO 99/18220 | * | 4/1999 |

OTHER PUBLICATIONS

Steller M. A., Current Opinion in Investigational Drugs, 2002, vol. 3, No. 1, pp. 37–47.*

Zhang, et al., "HPV6b virus like particles are potent immunogens without adjuvant in man", *Vaccine* 18 (2000), 1051–1058.

* cited by examiner

*Primary Examiner*—Ali R. Salimi
(74) *Attorney, Agent, or Firm*—Elliot M. Olstein; Raymond J. Lillie

(57) ABSTRACT

Disclosed are chimeric HPV L1 proteins and virus like particles comprising the same which are capable of generating high titer neutralizing antibody responses against at least two HPV types. The disclosed chimeric HPV L1 proteins and VLPs are useful as therapeutic and prophylactic reagents, as well as reagents for diagnosing papillomavirus infection.

5 Claims, 6 Drawing Sheets

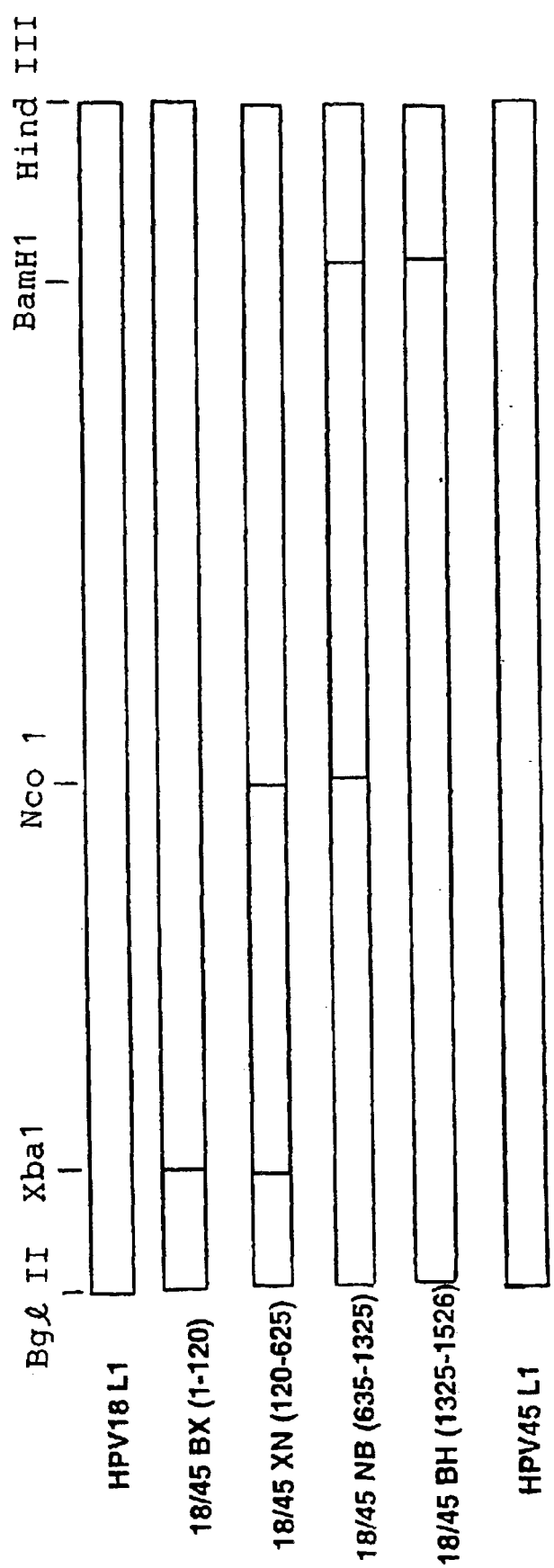

Figure 3:
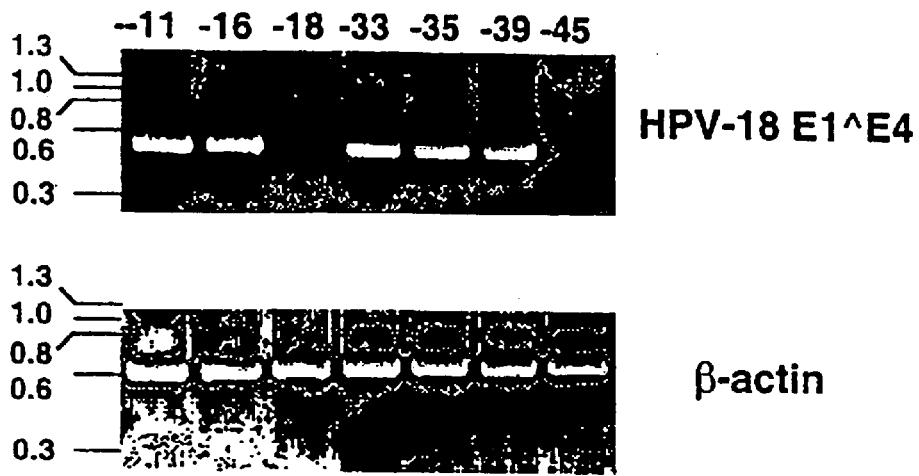

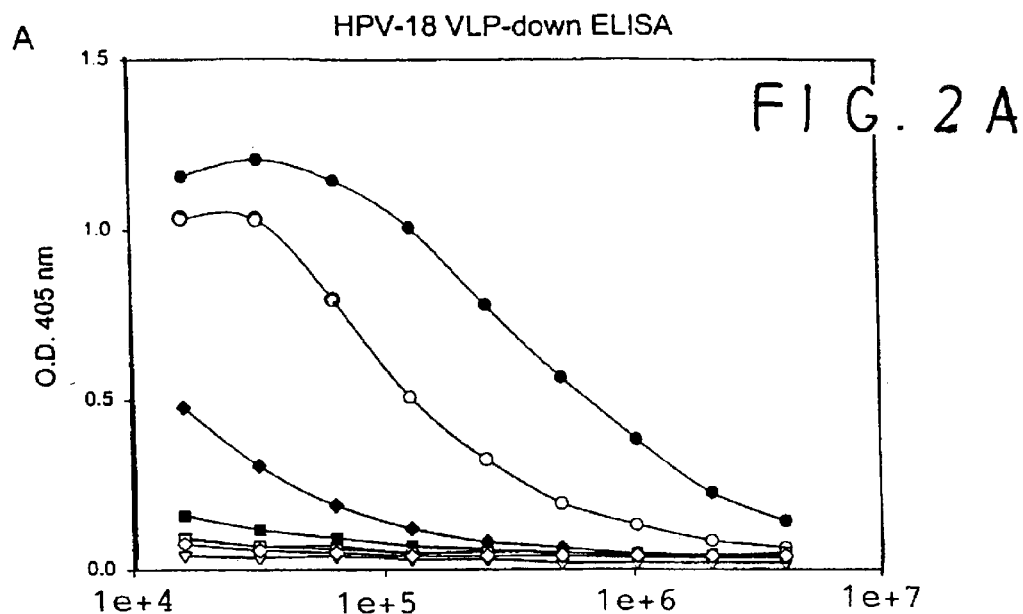
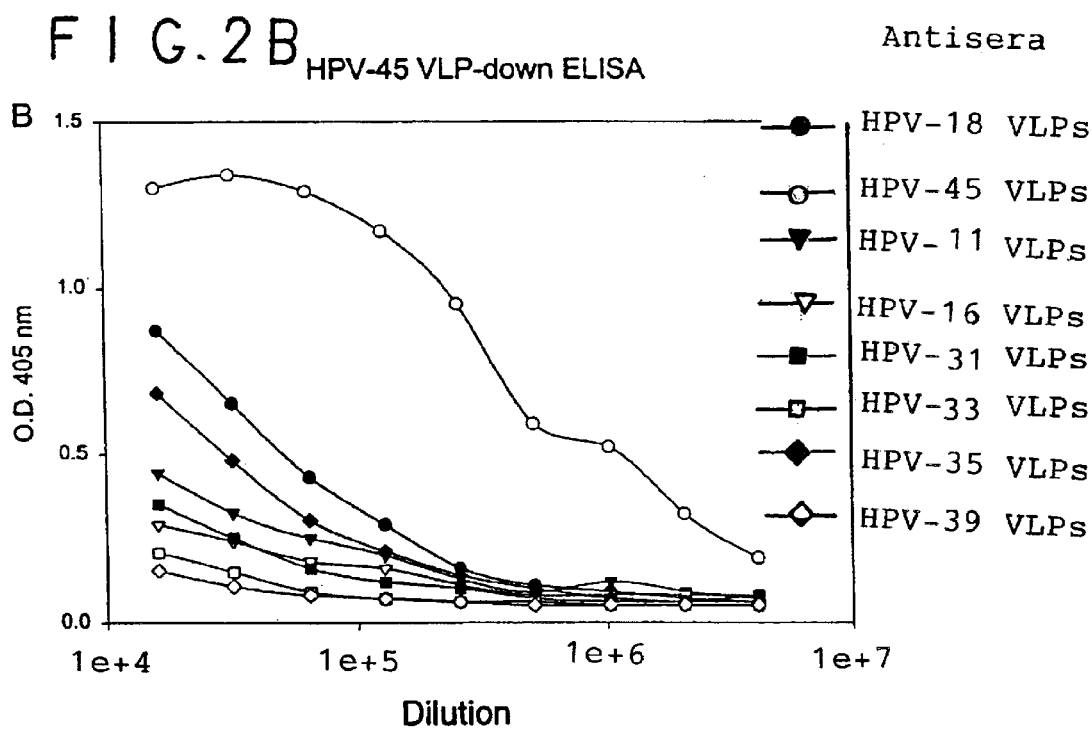
Antisera aginst a panel of HPV VLP types screened
18 VLPs (A) or HPV-45 VLPs B

HPV Type-Specific Antisera

Titration of the HPV-18 Neutralizing Activity in the anti-HPV-18 and HPV-45 VLP Sera F I G. 5
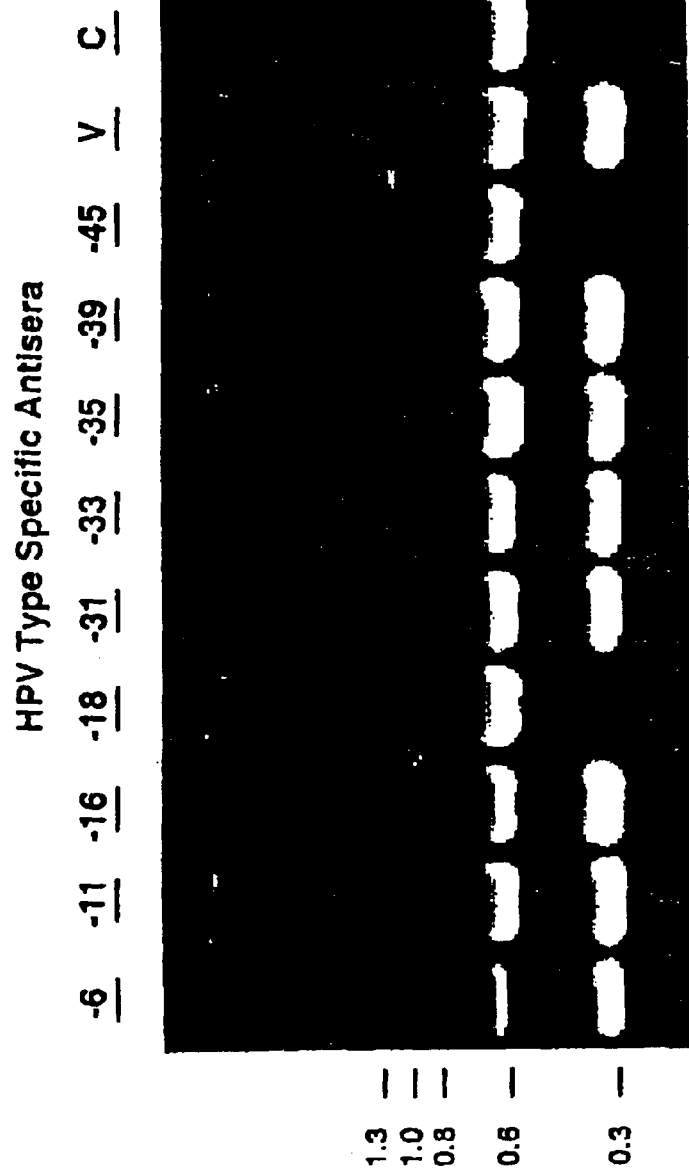

Binding of HPV-18 and HPV-45 reactive mAbs to 18/45 chimeric L1 VLPs

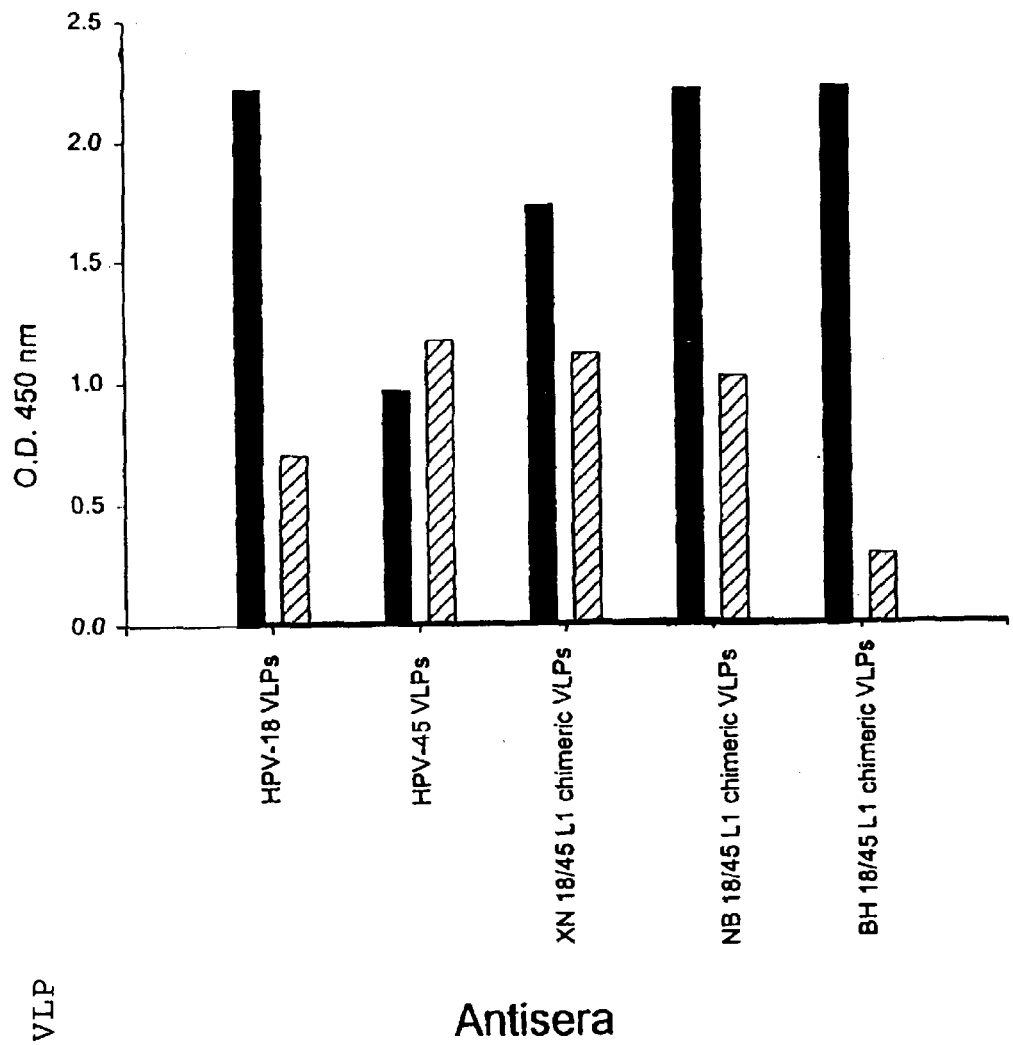

CHIMERIC HUMAN PAPILLOMAVIRUS (HPV) L1 MOLECULES AND USES THEREFOR

CROSS REFERENCE TO RELATED APPLICATION

This application claims priority from U.S. Provisional Ser. No. 60/212,839, filed Jun. 21, 2000, and is incorporated by reference herein in its entirety.

FIELD OF INVENTION

The present invention provides a means of generating high titered neutralizing antibody responses against two or more human papillomavirus (HPV) types with virus-like particles composed (VLPs) of a chimeric L1 molecule that contains neutralizing epitopes of each of the HPV types. These VLPs elicit neutralizing antibody responses and therefore may be used as effective prophylactic reagents against the disease states associated with prolonged infections with the HPV types. Cellular immune responses against the chimeric HPV L1 molecule may provide beneficial therapeutic effects against established infections. The chimeric VLPs may also be useful in the diagnosis of prior or current infection with the HPV types or be used as an aid in the determination of the level of protective (neutralizing) antibody present in a body fluid sample. Also, the present invention relates to the use of such VLPs for encapsulation of desired moieties, e.g., diagnostic or therapeutic agents, and the use thereof as "pseudovirions" for evaluating the efficacy of putative vaccines or therapeutics.

BACKGROUND OF THE INVENTION

Papillomaviruses infect a wide variety of different species of animals including humans. Infection is typically characterized by the induction of benign epithelial and fibroepithelial tumors, or warts at the site of infection. Each species of vertebrate is infected by a species-specific set of papillomavirus, itself comprising several different papillomavirus types. For example, more than sixty different human papillomavirus (HPV) genotypes have been isolated. Papillomaviruses are highly species-specific infective agents. For example, canine and rabbit papillomaviruses cannot induce papillomas in heterologous species such as humans. Neutralizing immunity to infection against one papillomavirus type generally does not confer immunity against another type, even when the types infect a homologous species.

In humans, papillomaviruses cause genital warts, a prevalent sexually-transmitted disease. HPV types 6 and 11 are most commonly associated with benign genital warts condylomata acuminata. Genital warts are very common, and subclinical or inapparent HPV infection is even more common than clinical infection. While most HPV-induced lesions are benign, lesions arising from certain papillomavirus types, e.g., HPV-16 and HPV-18, can undergo malignant progression. Moreover, infection by one of the malignancy-associated papillomavirus types is considered to be a significant risk factor in the development of cervical cancer, the second most common cancer in women worldwide. Of the HPV genotypes involved in cervical cancer, HPV-16 is the most common, being found in about 50% of cervical cancers. The prevalence of HPV-18 ranges from approximately 8–31% depending on the geographical location, and in most areas worldwide, HPV-45 is the third most frequent, oncogenic HPV type (Bosch, F. X., et al. (1995, J. Natl. Cancer Inst. 87: 796–802).

In view of the significant health risks posed by papillomavirus infection generally, and human papillomavirus infection in particular, various groups have reported the development of recombinant papillomavirus antigens and their use as diagnostic agents and as prophylactic vaccines. In general, such research has been focused toward producing prophylactic vaccines containing the major capsid protein (L1) alone or in combination with the minor capsid protein (L2). For example, Ghim et al, Virology, 190:548–552 (1992), reported the expression of HPV-1 L1 protein, using vaccinia expression in Cos cells, which displayed conformational epitopes and the use thereof as a vaccine or for serological typing or detection. This work is also the basis of a patent application, U.S. Ser. No. 07/903,109, filed Jun. 25, 1992 (abandoned in favor of U.S. Ser. No. 08/216,506, filed on Mar. 22, 1994), which has been licensed by the assignee of this application. Also, Suzich et al, Proc. Natl. Acad. Sci., U.S.A., 92:11553–11557 (1995), report that the immunization of canines with a recombinant canine oral papillomavirus (COPV) expressed in a baculovirus/-insect cell system completely prevented the development of viral mucosal papillomas. These results are important given the significant similarities between many HPVs and COPV. For example, COPV, similar to HPVs associated with anogenital and genital cancer, infects and induces lesions at a mucosal site. Also, the L1 sequences of COPV shares structural similarities to HPV L1 sequences. Given these similarities, the COPV/beagle model is useful for investigation of L1 protein-containing vaccines, e.g., investigation of the protective immune response, protection from natural infection and optimization of vaccination protocols. (Id.)

Also, a research group from the University of Rochester reported the production of human papillomavirus major capsid protein (L1) and virus-like particles using a baculovirus/insect cell expression system (Rose et al, University of Rochester, WO 94/20137, published on Sep. 15, 1994). In particular, they reported the expression of the L1 major capsid protein of HPV-6 and HPV-11 and the production of HPV-6, HPV-11, HPV-16 and HPV-18 virus-like particles.

Further, a University of Queensland research group also purportedly disclosed the recombinant manufacture of papillomavirus L1 and/or L2 proteins and virus-like particles as well as their potential use as vaccines (Frazer et al, WO 93/02189, published Feb. 4, 1993).

Still further, a United States government research group reported recombinant papillomavirus capsid proteins purportedly capable of self-assembly into capsomere structures and viral capsids that comprise conformational antigenic epitopes (U.S. Pat. No. 5,437,951, Lowy et al, issued Aug. 1, 1995). The claims of this patent are directed to a specific HPV-16 DNA sequence which encodes an L1 protein capable of self-assembly and use thereof to express recombinant HPV-16 capsids containing said HPV-16 L1 protein.

With respect to HPV capsid protein containing vaccines, it is widely accepted by those skilled in the art that a necessary prerequisite of an efficacious HPV L1 major capsid protein-based vaccine is that the L1 protein present conformational epitopes expressed by native human papillomavirus major capsid proteins (see, e.g., Hines et al, Gynecologic Oncology, 53:13–20 (1994); Suzich et al, Proc. Natl. Acad. Sci., U.S.A., 92:11553–11557 (1995)).

Both non-particle and particle recombinant HPV L1 proteins that present native conformational HPV L1 epitopes have been reported in the literature. It is known that L1 is stable in several oligomeric configurations, e.g., (i) capsomeres which comprise pentamers of the L1 protein and (ii) capsids which are constituted of seventy-two capsomeres in a T=7 icosahedron structure. Also, it is known that the L1 protein, when expressed in eukaryotic cells by itself, or in combination with L2, is capable of efficient self-assembly into capsid-like structures generally referred to as virus-like particles (VLPs).

VLPs have been reported to be morphologically and antigenically similar to authentic virions. Moreover, immunization with VLPs has been reported to elicit the production of virus-neutralizing antibodies. More specifically, results with a variety of animal papillomaviruses (canine oral papillomavirus and bovine papillomavirus-4) have suggested that immunization with VLPs results in protection against subsequent papillomavirus infection. Consequently, VLPs composed of HPV L1 proteins have been proposed as vaccines for preventing diseases associated with human papillomavirus infections.

For example, it has been reported that the L1 protein can assemble into VLPs when expressed using recombinant baculovirus and vaccinia virus vectors and in recombinant yeast (Hagensee et al, J. Virol., 68:4503–4505 (1994); Hofmann et al, Virology, 209:506–518 (1995); Kimbauer et al, Proc. Natl. Acad. Sci. USA, 89:12180–12184 (1992); Kimbauer et al, J. Virol., 67:6929–6936 (1993); Rose et al, J. Virol., 67:1936–1944 (1993); Sasagawa et al, Virology, 206:126–135 (1995); Suzich et al, Proc. Natl. Acad. Sci. USA, 92:11553–11557 (1995); Volpers et al, Virology, 200:504–512 (1994); Zhou et al, J. Virol., 68:619–625 (1994)).

Most previous recombinant L1 preparations isolated from eukaryotic cells have resulted in a variable population of VLPs approaching 55 nm in diameter, which are similar in appearance to intact virions. However, VLP assembly is somewhat sensitive to cell type. For example, L1 expressed in *Escherichia coli* is expressed largely in the form of capsomeres or smaller, with few or no capsids apparent either in the cell or upon purification (Rose et al, J. Virol., 67:1936–1944 (1993); Li et al, J. Virol., 71:2988–2995 (1997)). Similar results are observed when the polyoma virus VP1 protein is expressed in *E. coli* (Salunke et al, Biophys. J., 56:887–900 (1989)).

To date, there has been no effective method for eliciting high titered neutralizing antibody responses against two or more HPV types with a single VLP. Indeed, due to the rarity of authentic human papillomavirus stocks very little work has been conducted on cross-neutralizing antibody responses. However, the ability of HPV VLPs to elicit antisera that would cross-react with other HPV VLP types has been examined. Antisera to individual HPV VLP types have been tested by ELISA for reactivity with a variety of other HPV VLP types. In general, antibody reactivity to HPV VLPs is type-specific. The antiserum reacts with the VLP that was used in the generation of the antiserum but not with other HPV VLP types. In cases where a high degree of cross-reactivity of the antiserum with other VLP types have been reported, the amino acid sequences of the heterologous HPV type has been highly homologous to the original type. For example, strong anti-VLP antibody cross-reactions have been reported between HPV-6, HPV-11 and between HPV-18, HPV-45 (R. C. Rose, personal communication, W. White et al., in preparation, L. F. Zang (2000) Vaccine 1051–1058). The cross-neutralizing, activity of cross-reacting antisera has been assessed in the few instances where the HPV stocks are available and infectivity assays have been developed. In vitro infectivity assays for HPV-11, -16, -18 have been reported (Smith et al., 1995 J. Invest. Dermatol. 105: 1–7, White et al., 1998 J. Virol. 72:959–964, White et. al., 17th international Papillomavirus Conference, 1999). Additionally, assays for HPV-31 and -45 have been recently developed (S. Wilson, unreported results). Results with these assays have indicated that strong cross-reactivity is indicative of cross-neutralizing activity (White, et al., 1998 J. of Virol. 72: 959–964, White et. al., 17th International Papillomavirus Conference, 1999, Wilson, et al., unpublished results). In each case, however, the cross-neutralizing titer has always been significantly lower (10–100 fold) than the reactivity against the homologous type. The level of antibody that will be needed to provide protection against HPV infection is not known. However, it is a widely held belief that higher antibody titers will provide greater levels of protection. Thus, the current restriction is that broad-based coverage against a variety of HPV types will require the inclusion of multiple VLP types. Each additional VLP type represents production and purification challenges as well as increases the complexity and cost of the vaccine. Therefore, it would be advantageous to minimize the number of VLP types and yet produce a product capable of eliciting protective or therapeutic responses against a variety of HPV types.

SUMMARY OF THE INVENTION

The present invention provides a novel method for the induction of high titered neutralizing antibody responses or therapeutic cellular responses against two or more HPV types with a single chimeric L1 molecule. By creating a chimeric L1 VLP capable of eliciting antibody responses or cellular responses comparable to those induced by two or more individual VLP types, the methods of the invention diminish the need for a large number of VLP types in HPV VLP-based vaccines.

The novel chimeric HPV L1 VLPs of the present invention may be used for diagnosis of previous or current HPV infection and also to assess the level of protective antibody responses found in bodily fluids. Use of the chimeric molecule would thereby diminish the number of necessary tests and the number of necessary components required to define these parameters.

The chimeric HPV VLPs of the present invention may also be employed for encapsulation of desired moieties, e.g., diagnostic or therapeutic agents such as targeting ligands, antivirals, and radionuclides, and the use thereof as "pseudovirions" for delivering therapeutic agents to cells and evaluating the efficacy of putative vacacines or therapeutics.

BRIEF DESCRIPTION OF THE INVENTION

The amino acid sequences of the L1 proteins of HPV-18 and HPV-45 are highly homologous being 86% identical in amino acid sequence. HPV-18 L1 VLPs and HPV-45 VLPs elicit antisera which cross-react with one another (White et al., in preparation, Wilson et al., 18th International Papillomavirus Conference). In vitro infectivity assays have been developed with both HPV-18 stock (White et al., in preparation) and HPV-45 stock (Wilson et al., Abstract, 18th International Papillomavirus Conference), each stock a product of organotypic culture (Meyers et al. Abstract, 18th International Papillomavirus Conference). The infectivity assays were utilized to demonstrate that anti-HPV-18 VLP serum neutralizes both HPV-18 virus and HPV-45 virus. Also, anti-HPV-45 VLP serum neutralizes HPV-18 in addition to HPV-45. Thus, cross-neutralizing epitopes are present on both HPV-18 and HPV-45. However, in both instances, the potency of the antiserum to neutralize the homotypic virus was 100-fold greater than against the heterotypic virus.

As a means to generate a VLP which would elicit potent neutralizing titers against both virus types, four different chimeric HPV-18/45 L1 molecules were generated by exchanging segments of the L1 gene with homologous segments of the HPV-45 L1 gene. All four of the chimeric L1 molecules formed VLPs as demonstrated by electron microscopy. Each chimeric L1 VLP was tested by ELISA for reactivity with three HPV-18 neutralizing monoclonal antibodies (R5, J4, 195), which recognize distinct sites on HPV-18 L1 VLPs. One of the chimeric VLPs failed to bind monoclonal antibodies (mAbs) J4 and 195 but bound R5. Surprisingly, antisera generated in mice against this chimeric VLP displayed neutralizing titers against both HPV-18 and HPV-45 that were of comparable magnitude to those elicited by the homotypic VLPs. Although the J4 and 195 epitopes were lost, the maintenance of the R5 epitope (and perhaps other 18 epitopes) as well as the inclusion of HPV-45 neutralizing epitopes in a VLP format, provided the necessary structure for the induction of high titered neutralizing responses against both virus types. Thus, in summary, it has been found that a chimeric HPV L1 VLP consisting of amino acids 1–265 of HPV 18, followed by amino acids 265–442 of HPV 45, and ending with amino acids 443–507 from HPV 18 elicits high titered neutralizing responses against both virus types. These responses are of greater magnitude than those induced by either VLP type against the heterologous virus. Additionally, antibody responses against the J4 and 195 epitopes are not necessary for the induction of potent neutralizing responses against HPV-18. Based on these observations, it should be possible to provide functional chimeric L1 proteins with other HPV combinations, especially where there is a high level of homology, i.e., greater than about 75%, and a high level of cross-reactivity.

DEFINITIONS

Major capsid protein or L1 protein: the structural protein of papillomavirus (PV) which constitutes the major portion of the PV capsid structure. This protein has reported application in the preparation of HPV vaccines and as a diagnostic agent.

Virus-like particles or VLPs: the capsid-like structures which result upon expression and assembly of a papillomavirus L1 DNA sequence alone or in combination with an L2 DNA sequence. VLPs are morphologically and antigenically similar to authentic virions. VLPs may be produced in vivo, in suitable host cells, e.g., mammalian and insect host cells, or may form spontaneously upon purification of recombinant L1 proteins. Additionally, they may be produced using L1 fragments or mutated forms thereof, e.g. L1 proteins that have been modified by the addition, substitution or deletion of one or more amino acids. L1 mutants that fall within the scope of the present invention are those that upon VLP reassembly present at least one native PV conformational epitope. For example, this includes L1 proteins which have been truncated at the ultimate conserved glutamine residue at the carboxy-terminus. Cleavage at said glutamine residue will remove, on average, 30 to 40 amino acid residues of the L1 protein. Suitable mutants or fragments can be determined based on the reactivity of said L1 proteins with neutralizing antiserum or their ability to elicit neutralizing antiserum.

Correctly-folded L1 protein: L1 protein, fragment thereof or mutated form thereof, (either monomeric, in the form of small oligomers (dimers-tetramers) or capsomeres), which, upon expression, assumes a conformational structure that presents one or more conformational HPV L1 epitopes present on native viral capsids or VLPs and is suitable for assembly into VLPs. In the present invention, a correctly folded chimeric HPV L1 protein will present one or more HPV L1 conformational epitopes of each of the HPV types used to prepare the chimeric protein.

Conformational L1 HPV epitope: an epitope expressed on the surface of correctly-folded L1 protein which is also expressed by an L1 protein or fragment, or mutated form thereof, which is also expressed by an L1 protein of a corresponding wild-type, infectious HPV. It is well accepted by those skilled in the art that the presentation of conformational epitopes is essential to the efficacy (both as prophylactic and diagnostic agents) of HPV L1 protein immunogens.

Conformational Neutralizing L1 HPV epitope: an epitope expressed on the surface of correctly-folded L1 protein, fragment or mutated form thereof, which is also expressed by an L1 protein of a corresponding wild-type, infectious HPV, and which elicits neutralizing antibodies. It is well accepted by those skilled in the art that the presentation of conformational neutralizing epitopes is essential to the efficacy (both as prophylactic and diagnostic agents) of HPV L1 protein immunogens.

Conformational antibody: an antibody that specifically binds an epitope expressed on a correctly-folded L1 protein but not on denatured L1 protein.

Chimeric L1 molecule: the nucleotide sequence of one HPV type containing various segments of the analogous nucleotide sequence of an additional HPV type(s).

Chimeric VLP: a VLP composed of a chimeric L1 molecule.

BRIEF DESCRIPTION OF THE DRAWINGS

FIG. 1: Diagrammatic representation of the chimeric 18/45 L1 molecules. Restriction endonuclease sites were introduced into the HPV 45 L1 sequence by site directed mutagenesis, and the digested DNA fragments were used to replace homologous regions of HPV 18 L1. The numbers in parentheses indicates the location of the HPV 45 L1 gene sequence that was used to replace the 18 L1 gene.

FIG. 2A: Anti-VLP serum panel on HPV-18 VLPs. ELISA plates were coated with HPV-1 8 VLPs and reacted with serial 2-fold dilutions antisera generated in rabbits against the indicated HPV VLP types. Only the anti-HPV-18 sera and, to a lesser extent, the anti-HPV-45 sera exhibited significant binding to the HPV-18 VLPs over the dilution range examined.

FIG. 2B: Anti-VLP serum panel on HPV-45 VLPs. HPV-45 VLPs were coated to ELISA plates and reacted with the same panel of anti-HPV VLP antisera as in FIG. 2A. The results show that reactivity against the HPV-45 VLPs is largely type-specific; however, the anti-HPV-18 serum displayed the greatest degree of cross-reactivity.

FIG. 3: HPV-18 was preincubated with anti-HPV-11, -16, -18, -33, -35, -39, or -45 VLP sera and then added to HaCaT cells. HPV-18EIE4-specific and cellular -actin-specific RT-PCR products were generated with RNA isolated from the infected cells. The RNA and RT-PCR were performed essentially as described in White et. al., 1998, except that the HPV 18 specific forward outside primer was 5'GACTCCAACGACGCAGAGAAAC3' and the reverse outside primer was 5'GTCCACAATGCTGCTTCTCCG3'. The nested forward primer was 5'GTATGCATGG- ACCTAAGGCAAC3', and the reverse nested primer was 5'TCCACAGTGTCCAGGTCGTGT3'. Only the anti-HPV-18 and anti-HPV45 sera neutralized the virus.

Figure 4:
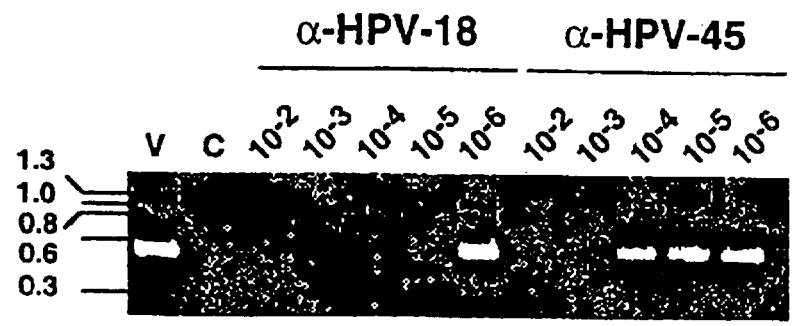

FIG. 4: Titration of anti-18 and anti-45 for HPV-18 neutralizing activity: HPV-18 was preincubated with preimmune rabbit serum diluted 1:100 (lane V), with serial log 10 dilutions of anti-HPV-18 VLP serum, or with serial log 10 dilutions of anti-HPV-45 VLP serum, prior to addition to keratinocytes. As a control, an additional aliquot of cells was incubated without virus (lane C). RT-PCR products obtained with total RNA and HPV-18-specific PCR primers as described in FIG. 3. The anti-HPV-18 VLP serum inhibited the detection of the EIE4 transcript at dilutions $1:10^5$, while the anti-HPV-45 serum only neutralized at dilutions of $1:10^3$.

FIG. 5: HPV-45 was preincubated with anti-HPV -6-11, -16, -18, -31-33, -35, -39, or -45 VLP sera and then added to HaCaT cells. HPV-45 EIE4-specific and cellular-actin-specific RT-PCR products were generated with RNA isolated from the infected cells. Only the anti-HPV-18 and anti-HPV45 sera neutralized the virus.

Figure 6:
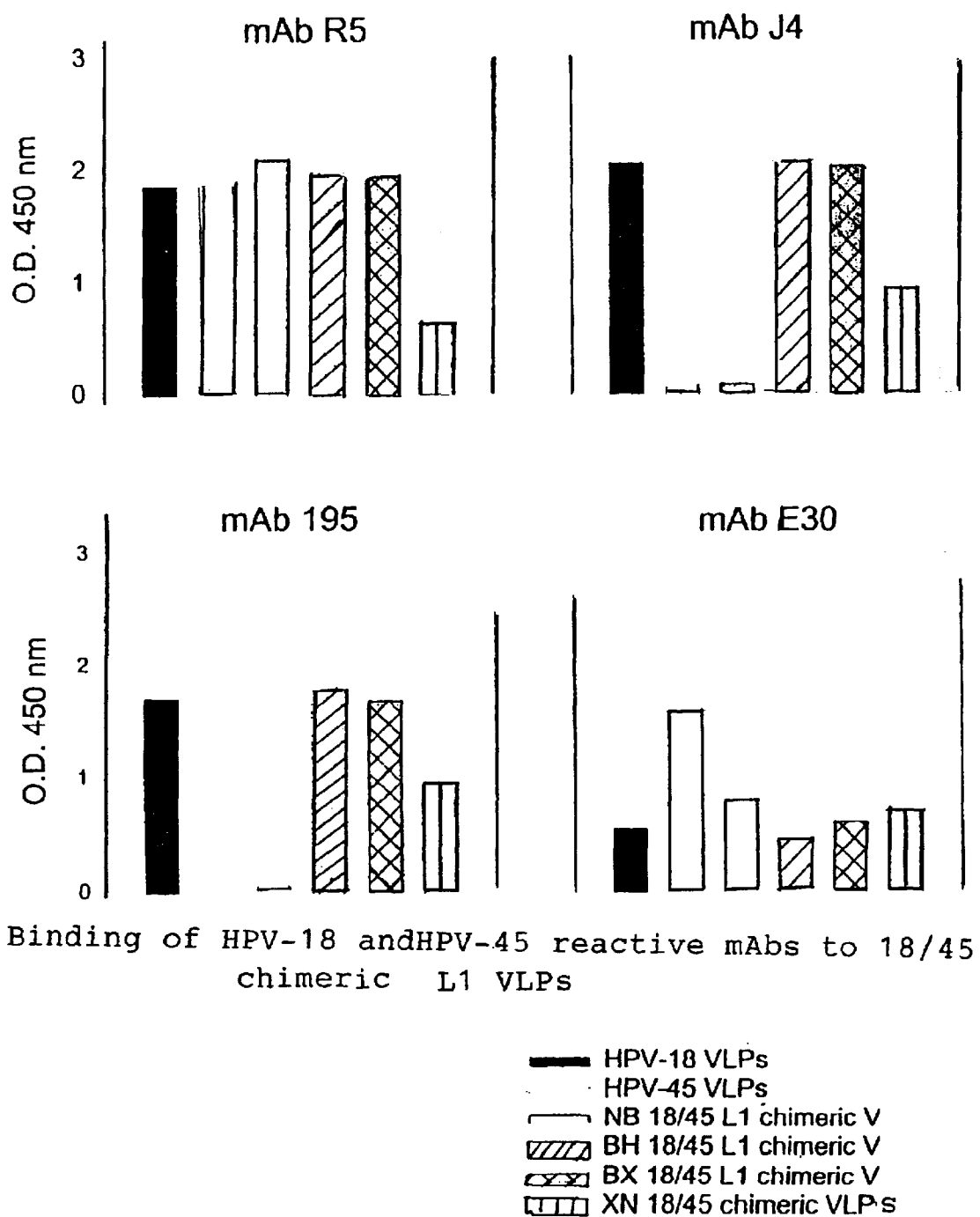

FIG. 6: Binding of HPV-18 and HPV-45 reactive mAbs to 18/45 chimeric L1 VLPs: HPV-18, HPV-45, or the 18/45 chimeric L1 VLPs were bound to microliter plates as described in the Materials and Methods. Ascitic fluids from the mAb-secreting hybridoma cell lines were diluted 1:128,000 and tested for binding reactivity against the various VLPs. MAbs R5, J4 and 195 are HPV-18 neutralizing. MAb E30 preferentially recognizes a conformational epitope on HPV-45 VLPs but also reacts less strongly with HPV-18 VLPs. Specific binding of the mAbs to the various VLPs was detected by a biotinylated anti-mouse Ig reagent through a colormetric readout generated by streptavidin horseradish peroxidase and substrate (TMB). Optical density readings were recorded at 450 nm after 15 minute incubation with the substrate and the addition of a stop reagent to terminate the color development. Averages of duplicate wells were calculated as the final O.D. values.

FIG. 7: Reactivity of polyclonal anti-chimeric 18/45 L1 VLP sera on HPV-18 and HPV-45 VLPs: Antisera to UPV-18,-45, and the XN, NB, and BH 18/45 L1 VLPs were generated in outbred Swiss mice. Five mice were immunized subcutaneously on weeks 0 and 3 with 2 μg of the indicated VLP adsorbed to aluminum hydroxide (1 mg/ml A1 final concentration). Antisera were collected on week 5 (two weeks after the secondary immunization). Pooled antisera from each group were diluted 1:4000 and tested for reactivity with HPV-18 or HPV-45 VLPs by ELISA. Specific binding was detected by a biotinylated anti-mouse Ig reagent through a colormetric readout generated by streptavidin horseradish peroxidase and substrate (TMB). Optical density readings were recorded at 450 nm after 15 minute incubation with the substrate and the addition of a stop reagent to terminate the color development. Averages of duplicate wells were calculated as the final O.D. values.

DETAILED DESCRIPTION OF THE INVENTION

The present invention provides for chimeric HPV L1 proteins that are capable of eliciting antibody responses or cellular responses comparable to those induced by two or more individual HPV types. This means that the chimeric proteins of the invention are capable of generating neutralizing titers against said two or more HPV types of a magnitude generally comparable to the neutralizing titer generated if each of said two or more HPV types had been administered separately. Generally comparable means that the neutralizing titer of the chimeric L1 protein and VLP against each virus type used to prepare the chimeric protein is at least 50% of the neutralizing titer generated against each homotypic virus. This is a significant improvement over the response generated by a single native HPV VLP (non-chimeric), where strong the cross-neutralizing activity, i.e. capability of the serum to neutralize HPV types other than the native type, is always significantly lower than the cross-reactivity of the serum, and the ability of the serum to neutralize heterotypic virus (about 100-fold lower with native L1 proteins and non-chimeric VLPs).

The chimeric HPV L1 proteins of the invention may be designed using sequences from any HPV type. Preferable HPV types are selected from the group consisting of HPV-11, -16, -18, -31, -33, -35, -39, and -45. Most preferable types will have a high level of homology, i.e., at least 65–75% amongst the native L1 genes, as is exhibited by HPV-6 and -11; HPV-16, -31, -33 and -35; and HPV-18, -45 and -39. In particular, said HPV types are HPV-16, -18, -31, -33 and -45. Where one of the L1 protein segments is from HPV-18, the chimeric HPV L1 protein preferably comprises at least the R5 epitope of HPV-18 , or at least amino acids 53–194 of HPV-18, or at least the N' terminus half (approximately amino acids 1–194) of HPV-18.

Any number of different HPV L1 gene segments may be joined together and would be included in the present invention so long as said chimeric molecule generated neutralizing serum against at least two epitopes from different HPV L1 proteins. However, the chimeric molecules of the present invention preferably generate neutralizing serum against all types of HPV used for construction of the chimeric molecule. One way to construct chimeric L1 proteins is to use a "tribrid" approach whereby three sections from L1 genes from different HPV types are joined, or the center section of one L1 gene is replaced from the corresponding region of another. A particularly preferred "tribrid" chimeric protein of the present invention comprises amino acids 1–265 of BPV-18, followed by amino acids 265–442 of HPV-45, and ends with amino acids 443–507 from HPV-18. However, the segments may be any length but preferably range from about 40 to about 400 amino acids.

Chimeric proteins containing conservative amino acid substitutions that do not affect the conformation of correctly folded proteins are also included. Such substitutions might be generated in the course of constructing the chimeric molecules depending on the conservation of restriction endonuclease sites. Such substitutions might also be generated for the purpose of increasing or creating neutralizing epitopes affective for other virus types.

The chimeric HPV L1 proteins of the present invention may be used to make virus like particles (VLP). Such VLPs may be used in vaccine compositions which further comprise pharmaceutical carriers and optionally adjuvants that are known in the art. The chimeric VLPs may also be used in therapeutic compositions for the treatment of patients with current papillomavirus infections. The VLPs, vaccines, therapeutic compositions and proteins of the invention may all be employed to generate high titer neutralizing antiserum to at least two HPV types.

High titer neutralizing activity means that said chimeric L1 protein is capable of eliciting antiserum that neutralizes at least two HPV types at a dilution of 1:1000, and more preferably at a dilution of 1:10,000. The neutralizing activity demonstrated against each virus type may vary depending on the level achieved by administering the native homotypic viruses, but is generally at least about 50% of the neutralizing activity generated by homotypic serum. The method may be used to induce high titer neutralizing antibody responses or cell-mediated immune responses against many different HPV types depending on the number of epitopes contained within a single chimeric L1 molecule. The number of HPV types against which antibody responses are generated can be further increased by administering VLPs comprising more than one chimeric L1 molecule. For instance, antisera against at least three HPV types can be generated by administering a VLP comprising at least two types of chimeric HPV L1 proteins so long as each type of chimeric molecule has at least one L1 epitope that is from a different HPV type than the other. Antisera generated by the methods described herein, as well as monoclonal antibodies derived therefrom are also part of the present invention.

The invention also includes genes which encode the chimeric HPV L1 proteins described herein. A gene that comprises coding sequences of HPV-18 preferably comprises at least the nucleotides of the native HPV-18 L1 gene which encode the R5 epitope, and more preferably at least about the N' terminus half of the native HPV-18 L1 gene. A preferred gene of the present invention comprises the native HPV-18 L1 gene wherein nucleotides 624 to 1327 have been replaced by the corresponding nucleotides of HPV-45. "Corresponding" means the nucleotides in the same position as those deleted when the two native genes are aligned in the most homologous manner. In "tribrid" virus types, the recombinant genes encoding the chimeric L1 proteins may have corresponding segments ranging from about 100 nucleotides to about 1200 nucleotides.

The invention also comprises vectors comprising the genes encoding the chimeric HPV L1 proteins, operably linked to regulatory sequences such as promoters, that drive their expression. HPV L1 sequences may be expressed in any host cell that provides for the expression of recoverable yields of HPV VLPs. Suitable host systems for expression of recombinant proteins are well known and include, by way of example, bacteria, mammalian cells, yeast, and insect cells. A preferred expression system comprises the baculovirus/insect cell system used in the examples as this system provides for high protein yields. However, HPV L1 and L2 proteins can be produced in other systems, in particular bacteria and yeast.

Suitable vectors for cloning of expression of the subject HPV L1 encoding DNA sequences are well known in the art and commercially available. Further, suitable regulatory sequences for achieving cloning and expression, e.g., promoters, polyadenylation sequences, enhancers and selectable markers are also well known. The selection of appropriate sequences for obtaining recoverable protein yields is routine to one skilled in the art.

The present invention also includes methods of vaccinating a subject against at least two types of HPV comprising administering a vaccine composition comprising at least one chimeric HPV L1 protein, wherein said at least one chimeric HPV L1 protein comprises neutralizing epitopes for at least two HPV types. Said at least two HPV types are preferably selected from the group consisting of HPV-11, -16, -18, -31, -33, -35, -39, and -45, but may be any HPV type. Preferably, the HPV types are HPV-18 and HPV-45. Where the vaccine composition includes HPV-18 epitopes, preferably the VLP displays at least the R5 epitope of HPV-18, or at least amino acids 53–194 of HPV-18, or at least the N' terminus half (approximately amino acids 1–194) of HPV-18. A preferred vaccine composition comprises a "tribrid" chimeric L1, which may contain segments of variable length from any three viruses. A preferred "tribrid" contains amino acids 1–265 of HPV-18, followed by amino acids 265–442 of HPV-45, and ending with amino acids 443–507 from HPV-18. The vaccine compositions may include either free chimeric L1 proteins, or VLPs comprising chimeric L1 proteins.

The vaccine compositions of the present invention may induce cellular immune responses as well as neutralizing antiserum titers. The compositions may include adjuvants or additional moieties for promoting cellular immune responses in addition to chimeric proteins or VLPs, i.e. cytokines or T cell receptor ligands. Such moieties may be admixed into the composition. Alternatively, the composition may be constructed whereby said moieties are incorporated into the VLP capsid. This may be done in vivo by incorporating moieties into VLPs as they are assembled inside the cell. Alternatively, this may be done by using reducing agents to affect disassembly and removal of the reagent to affect reassembly of the VLP. In this regard, the disclosure of Ser. No. 08/923,997 describes a method for the disassembly and reassembly of HPV VLPs for the purpose of incorporating agents to be delivered or to target VLPs to cells and is herein incorporated in its entirety.

The vaccines of the invention will contain an amount of the subject HPV VLPs sufficient to induce formation of neutralizing antibodies in the host contained in a pharmaceutically acceptable carrier. Administration of the subject VLP-containing vaccines may be effected by any pharmaceutically acceptable means, e.g., parenterally, locally or systemically, including by way of example, oral, intranasal, intravenous, intramuscular, and topical administration. The manner of administration depends on factors including the natural route of infection. The dosage administered will depend upon factors including the age, health, weight, kind of concurrent treatment, if any, and nature and type of the particular human papillomavirus. The vaccine may be employed in dosage form such as capsules, liquid solutions, suspensions, or elixirs, for oral administration, or sterile liquid formulations such as solutions or suspensions for parenteral or intranasal use. An inert, immunologically acceptable carrier is preferably used, such as saline or phosphate-buffered saline.

The vaccines will be administered in therapeutically effective amounts. That is, in amounts sufficient to produce a protective immunological response. Generally, the vaccines will be administered in dosages ranging from about 0.1 mg protein to about 20 mg protein, more generally about 0.001 mg to about 100 mg protein. Single or multiple dosages can be administered.

The methods of the present invention makes possible the preparation of HPV chimeric vaccines for preventing particular types of papillomavirus infection. For example, as more than one PV type may be associated with PV infections, the vaccines may comprise stable chimeric HPV VLPs derived from more than one type of PV. For example, as HPV 16 and 18 are associated with cervical carcinomas, therefore a vaccine for cervical neoplasia may comprise VLPs having chimeric L1 proteins designed from the L1 proteins of HPV 16 and HPV 18.

A variety of neoplasia are known to be associated with PV infections. For example, HPVs 3a and 10 have been associated with flat warts. A number of HPV types have been reported to be associated with epidermodysplasia verruciformis (EV) including HPVs 3a, 5, 8, 9, 10, and 12. HPVs 1, 2, 4, and 7 have been reported to be associated with cutaneous warts and HPVs 6b, 11a, 13, and 16 are associated with lesions of the mucus membranes (see, e.g., Kremsdorf et al, *J. Virol.,* 52:1013–1018 (1984); Beaudenon et al, *Nature,* 321:246–249 (1986); Heilman et al, *J. Virol.,* 36:395–407 (1980); and DeVilliers et al, *J. Virol.,* 40:932–935 (1981)). Thus, the subject vaccine formulations may comprise chimeric VLPs derived from different HPV types depending upon the desired protection.

The present invention also includes methods of treating a papillomavirus infection characterized by more than one HPV type comprising administering a therapeutic composition comprising HPV VLPs displaying at least one chimeric L1 proteins. Also included are methods of treating a papillomavirus infection caused by a first HPV type, concurrently with prophylactically treating at least one other type of HPV infection comprising administering a therapeutic composition comprising HPV VLPs displaying at least one chimeric L1 protein.

The therapeutic methods of the present invention further provide for the introduction of desired moieties, e.g., DNAs, proteins, peptides, hormones, radionuclides, anti-cancer agents and antiviral agents into VLPs during reassembly. This is advantageous as such VLPs may be used as delivery vehicles (for insertion of desired moieties into cells) and as "pseudovirions" for evaluating the prophylactic efficacy of papillomavirus vaccines.

For example, the moieties that may be encapsulated in the VLPs include therapeutic and diagnostic moieties, e.g., nucleic acid sequences, radionuclides, hormones, peptides, antiviral agents, antitumor agents, cell growth modulating agents, cell growth inhibitors, cytokines, antigens, toxins, etc. The subject VLPs, which contain a desired moiety encapsulated therein, upon administration to a desired host, preferably human, should be taken up by cells normally infected by the particular papillomavirus, e.g., epithelial cells, keratinocytes, etc., thereby providing for the potential internalization of said encapsulated moiety into these cells. This may facilitate the use of the subject VLPs for therapy (as opposed to prophylatics) because it enables the delivery of a therapeutic agent into a desired cell site, e.g., a cervical cancer site. Given the fastidiousness of PVs in general, this may provide a highly selective means of delivering desired moieties to target cells. For example, it may provide a means of delivery of nucleic acid sequences, e.g., a DNA encoding a therapeutic polypeptide, or an antisense sequence.

The moiety or moieties encapsulated, of course, should not adversely affect VLP assembly and/or stability. This may be determined by producing VLPs containing the desired moiety and assessing its effects, if any, on VLP assembly and/or stability.

In the case of DNAs or RNAs, the encapsulated nucleic sequence can be up to 8 kilobases, the size of the PV genome. However, typically the encapsulated sequences will be smaller, e.g., on the order of 1–2 kilobases. Typically, these DNAs will encode a desired polypeptide, e.g., therapeutic polypeptide, such as an enzyme, hormone, growth factor, etc. This sequence will further be operably linked to sequences that facilitate the expression thereof in the targeted host cells.

Another application of chimeric VLPs containing encapsulated DNAs are as "pseudovirions". In this regard, numerous papillomaviruses, including those involved in human diseases, are rare, cannot be propagated readily in vitro and cannot be easily purified from human cell sources in amounts that facilitate the use thereof in antibody neutralization assays. This is problematic, as it prevents or makes difficult evaluating the feasibility of vaccines or therapeutics for protection against these specific HPV viruses. The present invention should obviate or at least reduce such problems.

Essentially, chimeric "pseudovirions" will be constructed which comprise VLPs which are constituted of a chimeric L1 or a combination of chimeric L1 and L2 proteins of the particular PV, and further encapsulated therein part of the genome of said papillomavirus or a DNA encoding a selectable marker. This pseudovirion will be used in an in vitro cell "infectivity" assay to evaluate efficacy of corresponding VLP vaccines. Essentially, this will be effected by contacting cells with such pseudovirions. These pseudovirions should bind such cells and provide for the insertion of said DNA. Thereafter, insertion of said DNA may be evaluated by known methods, e.g., PCR hybridization methods, or based on the expression of the selectable marker, e.g., -galactosidase.

This will be effected both in the presence and absence of antibodies generated against L1 or L2 proteins specific to the particular HPV used to make the chimeric VLP. If insertion is inhibited, as determined, e.g., based on reduced expression of the selectable marker, this is an indication that the L1 or L2 protein elicited production of virus-neutralizing antibodies.

The invention further includes methods of making a multi-HPV type vaccine or therapeutic composition comprising (a) ligating together portions of the native L1 genes encoding for the different epitopes;

(b) cloning the ligated gene portions into an expression vector; and (c) expressing the vector in a cell line which allows the formation of VLPs, wherein said VLPs display at least one L1 neutralizing epitope from at least two different HPV types.

PCR may be used to create compatible overhangs on the ends of L1 gene portions to permit ligation of gene portions following restriction endonuclease digestion. Alternatively, restrictions sites existing in the native sequences of HPV L1 proteins may be used to join L1 portions of different HPV types.

The present invention also includes methods of diagnosing prior or current papillomavirus infection comprising (a) isolating serum from a patient suspected of having a prior or current papillomavirus infection;

(b) exposing an immobilized chimeric HPV L1 protein to said serum as to allow binding interaction between the HPV L1 epitopes and the antiserum while at the same time separately exposing the identical chimeric HPV L1 to an irrelevant antiserum or antibody;

(c) washing said immobilized chimeric HPV L1 such that unbound components are separated;

(d) exposing said washed chimeric HPV L1 protein to a labeled reagent that binds with specificity to immunoglobulins of said patient; and (e) comparing the amount of label bound to each chimeric HPV L1 sample.

The chimeric HPV L1 proteins may be incorporated into VLPs, and either the chimeric proteins or VLPs may be immobilized on beads, the surface of a tissue culture dish or cells through a binding interaction with L1 or VLP specific antibodies. Label bound to cells may be measured by flow cytometry or any other routine means known in the art. Alternatively, serum components may be bound and thereafter exposed to chimeric VLPs, the binding of which is then detected with L1 antibodies specific for the L1s of the virus types used to make the chimeric protein. The method permits antibodies for at least two different HPV types to be screened simultaneously using two different labeled reagents.

When used for diagnosis or serotyping, chimeric VLPs according to the invention may be labeled using any of a variety of labels and methods of labeling. Examples of types of labels which can be used in the present invention include, but are not limited to, enzyme labels, radioisotopic labels, non-radioactive isotopic labels, fluorescent labels, toxin labels, and chemiluminescent labels.

Examples of suitable enzyme labels include malate hydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholineesterase, etc.

Examples of suitable radioisotopic labels include $^3H$, $^{125}I$, $^{131}I$, $^{32}P$, $^{35}S$, $^{14}C$, $^{51}Cr$, $^{57}To$, $^{58}Co$, $^{59}Fe$, $^{75}Se$, $^{152}Eu$, $^{90}Y$, $^{67}Cu$, $^{211}At$, $^{212}Pb$, $^{47}Sc$, and $^{109}Pd$.

Examples of suitable fluorescent labels include a $^{152}Eu$ label, a fluorescein label, an isothiocyanate label, a rhodamine label, a phycoerythrin label, a phycocyanin label, an allophycocyanin label, an o-phthaldehyde label, a fluorescamine label, etc.

Examples of suitable toxin labels include diphtheria toxin, ricin, and cholera toxin. Examples of chemiluminescent labels include a luminal label, an isoluminal label, an aromatic acridinium ester label, an imidazole label, and acridinium salt label, an oxalate ester label, a luciferin label, a luciferase label, an aequorin label, etc.

Those of ordinary skill in the art will know of other suitable labels which may be employed in accordance with the present invention. The binding of these labels to VLPs can be accomplished using standard techniques commonly known to those of ordinary skill in the art. Typical techniques are described by Kennedy et al, *Clin. Chim. Acta*, 70:1–31 (1976), and Schurs et al, *Clin. Chim. Acta*, 81:1–40 (1977). Coupling techniques mentioned in the latter are the glutaraldehyde method, the periodate method, the dimaleimide method, the m-maleimidobenzyl-N-hydroxysuccinimide ester method, all these methods incorporated by reference herein.

The detection of the anti-HPV antibodies using the subject chimeric VLPs can be improved through the use of carriers. Well-known carriers include glass, polystyrene, polypropylene, polyethylene, dextran, nylon, amylases, natural and modified celluloses, polyacrylamides, agaroses and magnetite. The nature of the carrier can be either soluble to some extent or insoluble for the purposes of the present invention. Those skilled in the art will note many other carriers suitable for binding proteins, or will be able to ascertain the same by use of routine experimentation.

Having now generally described the invention, the following materials and methods and examples are offered by way of illustration and not intended to be limiting unless otherwise specified.

Materials and Methods

ELISA for detection of mouse anti-HPV-VLP antibodies: HPV-18 L1 and HPV-45 L1 VLPs were heterologously expressed in *Trichoplusia ni* (High Five®) cells infected with recombinant baculovirus encoding the complete L1 sequence downstream of the polyhedrin promotor as described (Ghim et al, In M. A. Stanley (ed.) Immunology of human papillomaviruses, Plenum, N.Y., p. 147–153 (1993)). Cells were harvested approximately 72 hours post-infection, pelleted by centrifugation and frozen. Alternately, VLPs were isolated from fresh cell paste which was not frozen. To isolate the VLPs, the cell paste was resuspended in homogenization buffer (20 mM $NaH_2PO_4$, 150 mM NaCl, pH 7.4, containing leupeptin, 1 ug/ml aprotinin and 50 uM Pefabloc®) and lysed in a microfluidizer (Microfluidics model HC8000/3A)). The homogenized lysate was then centrifuged at 100,000×g for 90 minutes and the pellet containing the HPV-18 or HPV-45 VLPs was resuspended in PBS containing CsCl (405 g/L). The clarified lysate was then centrifuged overnight at 83,000×g and the VLP band was collected. The VLPs were diluted in PBS-0.5M NaCl and layered over a two component step gradient composed 30% and 65% sucrose. The gradients were centrifuged at 167,000×g for 3 hours and then the purified VLP band was collected at the interface between the two sucrose solutions. The VLPs were then dialyzed into PBS-0.5M NaCl. Protein concentration was determined by the Bradford assay (Bradford et al., Anal. Biochem. 72: 248–54 (1976)) using BSA as the reference protein and the L1 content was determined as described (Suzich et. al., PNAS, 92: 115553–11557 (1995)). Purified VLPs were aliquoted and stored at −80° C. until used.

VLPs (either HPV-18 or HPV-45) were diluted in PBS to 800 ng/ml and 100 l aliquots were dispensed into 96-well microliter plates (NUNC Maxisorp, Nalge Nunc International, Denmark). Plates were incubated at 2–8 C. overnight and then washed with PBS with 0.1% Tween 20. All subsequent steps were conducted at 20 C. Plates were blocked for 1 hour with 5% nonfat dry milk in PBS. Following washing, serial two-fold dilutions of anti-VLP sera or ascites fluid containing anti-HPV-18 or HPV-45 monoclonal antibodies (mAbs) in 1% nonfat dried milk were added to the wells in duplicate. Normal serum samples or ascites fluid containing an irrelevant mAb were used as negative controls. After a two hour incubation, the plates were washed and 1:3,000 dilution of biotinylated sheep anti-mouse Ig (Amersham Pharmacia Biotech, Piscataway, N.J.) in 1% BSA was added to the plates. The plates were incubated for one hour, washed and a 1:2,000 dilution of streptavidin-biotinylated horseradish peroxidase in 1% BSA was distributed to each well. Following a one hour incubation, the plates were washed and developed with TMB [3,3',5,5'-tetramethylbenzidine] (Bio-Rad Laboratories, Hercules, Calif.) diluted 1:2 in 0.1 M sodium citrate, 0.1 M acetic acid pH 5.8. After 15 minutes of incubation, the enzymatic reaction was stopped with 0.2 M $H_2SO_4$. Optical density (O.D.) readings were taken at 450 nm. Averages of duplicate wells were calculated as the final O.D. values.

ELISA for detection of rabbit anti-HPV-VLP antibodies: A panel of antisera against HPV-11, 16, -18, -31, -33, -35, 39, and 45 VLPs was generated in rabbits as previously described (White et al., J. Virol. 72: 959-964, 1998). HPV-18 or HPV-45 VLPs were coated onto microliter plates as described above. The plates were washed, blocked and the primary antisera were diluted in the same manner as the ELISA for the mouse antibodies. The rabbit VLP-specific antibodies were detected with goat anti-rabbit IgG (heavy and light chain specific, Kirkegaard and Perry Laboratories, Inc., Gaithersburg, Md.) diluted 1:8,000 in 1% milk in PBS. After 1 hour incubation, the plates were washed and specific binding was detected with ABTS (Kirkegaard and Perry Laboratories, Inc., Gaithersburg, Md.). Optical density readings were conducted at 405 nm at the 30 minute endpoint. Averages of duplicate wells were calculated as the final O.D. readings.

Monoclonal Antibody Binding to HPV-18 L1 VLPs: Surface Plasmon Resonance (BIACORE):

All steps were performed at 25 C. CM5 sensor chips (BIACORE, Inc. Pistataway, N.J.) were activated with N-hydroxysuccinimide/1-ethyl-3-[3-dimethylaminopropyl]-carboduimide as directed by the manufacturer. A 400 nM solution of purified 114K HPV-16 VLPs in 10 mM sodium acetate, pH 5 was injected over an activated chip (Karlsson, R. and A. Fält, J. Immunol. Methods 200:121–133, 1997). Unreacted ester groups were then blocked with 1 M ethanolamine. Binding studies were conducted with ascites from the R5, J4, and 195 hybridoma cell lines diluted with HEPES buffered saline, pH 7.4. Approximately 100 1 of dilute ascites was injected onto the VLP-coupled sensor chip at a flow rate of 10 l/min. Binding was indicated as a change in resonance units on the chip. An anti-HPV-16 mAb was used as a control for non-specific binding. For pair-wise competitive binding studies, a saturating amount of one mAb was passed over the VLP-coupled sensor chip followed by an injection of the same or a different mAb. Following each binding cycle, the VLP-coupled surface was regenerated with 3 M $MgCl_2$.

Electron microscopy: Protein samples were allowed to settle on formvar-and-carbon-coated grids (Electron Microscopy Sciences), blotted dry and stained with freshly-filtered 2% phosphotungstic acid, pH 6.8. Grids were examined in a JEOL model 1005 transmission electron microscope at an acceleration voltage of 100 KV and photographed at nominal magnifications of 15-25,000×.

Construction of Baculovirus Transfer Vector containing HPV 18L1 and HPV 45 L1: The HPV 18 L1 gene was amplified by PCR, placing a BglII site before the initiation codon and a HindIII site distal to the stop codon. The PCR product was cloned into the pCR2.1. (In Vitrogen) and the sequence was confirmed by automated DNA sequencing. A similar strategy was used to clone the HV45 L1 gene into pCR2.1. To produce a baculovirus transfer vector, the 1.5 Kb 18 L1 gene was excised from the pCR 18L1 plasmid using the restriction endonucleases BglII and HindIII, purified by agarose gel electrophoresis, and ligated into pFastBac (LifeTechnologies) which had been digested with BamHI and HindIII. This clone was designated pFB 18 L1. An identical strategy was used to subclone the HPV 45 L1 gene into pFastBac. This clone was designated pFB 45 L1.

Construction of HPV 18/45 Chimera L1 Genes: A total of four recombinant baculoviruses containing chimeric HPV 18/45 L1 series were constructed. Three recombinant baculovirus containing HPV 18/45 L1 chimera genes were constructed using site directed mutagenesis to place restriction sites in the HPV 45 L1 gene to match specific sites found in the HPV 18 L1 gene. The fourth chimeric VLP took advantage of a restriction site that occurred in both sequences. Table 1 shows the sequences of the oligonucleotides used to place restriction endonuclease sites into the HPV-45 L1 coding sequence. Restriction fragments were used to replace homologous regions in the HPV-18 L1 coding sequence to produce chimeric L1 genes.

TABLE 1

PCR Primers Used For Construction of HPV 18/45 Chimeric L1 Genes

| L1 Gene | Forward PCR Primer | Reverse PCR Primer |
|---|---|---|
| HPV 18 L1 | 5'CAGATC<u>AGATCTATG</u><br>      BglII Met<br>GCTTTGTGGCGGCCTAGTG3' | 5'TATGC<u>AAGCTTACTT</u><br>      HindIII Stop<br>CCTGGCACGTACACGCAC3' |
| HPV 45 L1 | 5'CCATAG<u>AGATCTATG</u><br>      BglII Met<br>GCTTTGTGGCGGCCTAGT3' | 5'AAGCG<u>AAGCTTATTT</u><br>      HindIII Stop<br>CTTACTACGTATACGTAC3' |
| 18/45 L1 BX | 5'CCATAG<u>AGATCTATG</u><br>      BglII Met<br>GCTTTGTGGCGGCCTAGT3' | 5'CAAGAA<u>TCTAG</u>AACT<br>      XbaI<br>GCCTGCATGATAAAA3' |
| 18/45 L1 XN | 5'AGGCAGT<u>TCTAGA</u>TT<br>      XbaI<br>ATTAACTGTAGGCAA3' | 5'ACTAAAAT<u>CC</u>ATGGC<br>      NcoI<br>CCCATAACCTGTATCCAC3' |
| 18/45 L1 NB | 5'TTGG<u>CC</u>ATGGATTTT<br>      NcoI<br>AGTACATTGCAGG3' | 5'AAGCG<u>AAGCTTATTT</u><br>      HindIII Stop<br>CTTACTACGTATACGTAC3' |

To produce the gene designated 18/45 BX, oligonucleotides homologous to HPV 45 L1 were synthesized to place a Bgl 11 site proximal to the initiation codon in the forward primer and an XbaI site was created by changing the C at nucleotide position 120 to a T and the C at nucleotide 121 to an A in the reverse primer. These primers were used to amplify a 125 base pair fragment using the HPV 45 L1 gene as template. The resulting amplicon was digested with BglII and XbaI and used to replace the homologous fragment of the HPV 18 L1 gene. The pCR 18 L1 clone was digested with XbaI and HindIII and the 1.4 Kb fragment was isolated by agarose gel electrophoresis. A three way ligation was then performed using the Baculovirus transfervector pFastBac (Life Technologies) which had been digested with BamHI and HindIII, the HPV 45 amplicon digested with Bgl II and XbaI and the HPV 18 L1 fragment that had been digested with XbaI and HindIII. The resultant chimera gene, which consists of the first 122 nucleotides of HPV 45 followed by 1403 nucleotides of the HPV 18 L1 gene, which codes for three amino acid changes from the HPV 18 L1 parental sequence.

To produce the gene designated 18/45 XN, a forward PCR primer was designed to place anXbaI in the HPV 45 L1 gene by changing the C at position 120 to a T and the C at position 121 to an A. The reverse primer was designed to place an NcoI site in the HPV 45 L1 gene by changing the A at nucleotide position 624 to a C. A 502 base pair fragment was amplified using these primers and HPV45 L1 as template by PCR. The resultant amplicon was digested with NcoI and XbaI. The pFB 18 L1 plasmid was digested with XbaI and HindIII and the 5.8 Kb fragment was purified by agarose gel electrophoresis. The 5.8 Kb fragment was ligated with the 502 bp PCR product that had been digested with XbaI and NcoI. The resultant clone consisted of the HPV 18 L1 gene with nucleotides 120 to 623 replaced by HPV 45 L1.

To produce the gene designated 18/45 NB, a forward PCR primer was designed to place an NcoI site in the HPV 45 L1 gene by substituting a C at position 624. The reverse primer required no base changes, because the wild type HPV 45 L1 gene contained a BamHI site. Therefore the reverse primer used to created the full length HPV 45 L1 gene was used with the NcoI forward primer to amplify a 900 base pair fragment by PCR. The PCR product was digested with NcoI and BamHI and the 702 base pair fragment was purified by agarose gel electrophoresis and ligated with the 5.6 Kb fragment of the pFB 18 L1 plasmid that had been digested with NcoI and BamHI. The resultant clone contained the HPV 18 L1 gene with nucleotides 624 to 1327 replaced by the HPV 45 L1 gene.

To produce the gene designated 18/45 BH, the pFB18L1 plasmid was digested with BamHI and HindIII and the 6 Kb fragment was gel purified by agarose gel electrophoresis. The pFB45L1 plasmid was also digested with BamHI and HindIII and the 0.2 Kb fragment was purified by agarose gel electrophoresis. The 6 kb and the 0.2 Kb fragments were ligated to produce the plasmid containing the HPV 18 L1 gene with nucleotides 1328 to 1524 replaced by the HPV 45 L1 gene.

Recombinant baculoviruses encoding the various L1 genes were produced using the Bac to Bac System (Life Technologies, Rockville, Md.) according to manufacturers recommendations.

HPV-18 and HPV-45 neutralization assays: Antisera against HPV 18 VLPs, HPV 45 VLPs an HPV 18/45 chimeric VLPs were generated in Swiss Webster mice. The mice (5 per group) were injected subcutaneously with 2 g of VLPs adsorbed to aluminum hydroxide adjuvant (Alhydrogelg, E. M. Sergeant Pulp and Chemical Co., Inc., Clifton, N.J.) at weeks 0 and 3 and serum samples were collected on week 5. To determine whether the antisera raised in the mice was able to neutralize HPV 18 and HPV 45 virus, the ability of the antisera to block the expression of a specific HPV 18 or HPV 45 spliced mRNA in a human cell line (HaCaT) was tested.

HaCaT, an immortalized human keratinocyte cell line (Boukamp et al, J. Cell Biol, 106:761–771 (1988)) were provided by Dr. Norbert Fusenig. Cells were grown to confluence in DMEM (LifeTechnologies) supplemented 10% Fetal Bovine Serum, 2 mM glutamine, 1 mM pyruvate, penicillin (100 units/ml), and streptomycin (100 μg/ml) in 24 well plates. HPV 18 or HPV 45 virus stock (provided by Craig Meyers, Abstract, 18$^{th}$ International Papillomavirus Conference) was sonicated for 30 seconds on ice. The stocks were then diluted 1:800 for HPV 18 or 1:500 for HPV 45 in medium and mixed with antisera which had been serially diluted 10 fold in medium to a final volume of 0.5 ml. The virus/antisera mixture was incubated for one hour at 37 C. Medium was aspirated from the HaCaT cells and the virus/ antisera mixture was added to the well. As a control, one well of cells on each plate received 0.5 ml of medium without virus. The cells were co-cultured with the virus/ antisera mixtures for 48 hours at 37 C., at which time mRNA was purified from the cells using the mRNA capture kit (Roche Molecular Biochemicals, Indpls., Ind.). The medium was aspirated from the cells and the cells were washed two times will 0.5 ml of ice cold 1× PBS. The final wash was aspirated from the cells and 0.25 ml lysis buffer was added to each well and the cell lysate was transferred to a RNase free microfuge tube. The cell lysates were sonicated for two minutes in a cup horn sonicator on ice to reduce the viscosity of the lysate. Biotinylated oligo dT was diluted 1:4 with nuclease free H$_2$O and 1 l was added to each lysate. Samples were incubated 10 minutes at 42 C. to allow the oligo dT to anneal to the mRNA. A 50 1 aliquot of the lysate was transferred to a streptavidin coated PCR tube and incubated for three minutes at 37 C. The lysates were removed from the PCR tubes and discarded. The RNA captured in the tubes was washed three times with 200 1 of wash buffer. Excess wash buffer was removed from the tubes with a micropipet tips. The ability of the antisera to block the expression of HPV 18 and HPV 45-specific spliced mRNA was determined by reverse transcriptase (RT)-PCR. RT reactions were performed using reagents from the First Strand cDNA kit (Roche Molecular Biochemicals). A master mix was prepared so that each reaction contained 5 1 10× buffer, 5 1 dNTPs, 10 1 MgCl2, 1 1 gelatin, 2 1 RNase Inhibitor, 2 1 AMV-RT, in a final volume of 50 1. Fifty microliter aliquots of the master mix were transferred to the PCR tubes containing the captured mRNA. Samples were placed in a thermalcycler and incubated for two hours at 42 C. The cDNA reaction mix was then removed from the PCR tubes and discarded. The cDNA captured in the PCR tubes was washed with 200 1 of wash buffer. Nested PCR was needed to detect the HPV EIE4 cDNA. The first round of amplification was carried out by adding a PCR mix to the captured cDNA, utilizing 5'GTTGTGTATGTGTTGTAAGTGTGA3' (located at nucleotide 786-810 in the HPV 18 genome) as the forward primer and 5'GTCCACAATGCTGCTTCTCCG3' (located at nucleotide position 3580–3600 in the HPV 18 genome) as the reverse primer for 40 cycles of PCR. Ten percent of the first round PCR mixture was used for nested reactions with 5'GAATTGAGCTAGTAGAAAGCT3' (located at nucleotide position 816–840 in the HPV 18 genome) as the nested forward primer and 5'TCCACAGT-GTCCAGGTCGTGT3' (located at nucleotide position 3666–3575 in the HPV 18 genome) as the nested reverse primer for 40 cycles of PCR. A similar set of nested PCRs was performed for the detection of the HPV 45 EIE4 spliced message. Forty cycles of PCR was performed on the cDNA synthesized from HPV 45 infected HaCaT cells, using 5'GAGCTTACAGTAGAGAGCTCG3' (located at nucleotide position 806–826 in the HPV 45 genome) as the forward primer and 5'TGTTACCACTACACACTTTC-CTTC3' (located at nucleotide position 3613–3636 in the HPV 45 genome) as the reverse primer. The nested amplification was performed using 10 per cent of the first PCR mixture as template utilizing 5'GCAGAGGACCTTAGAA-CACTA3' (located at nucleotide position 827–847 in the HPV 45 genome) as the forward nested primer and 5'GAA-CACAGGAGCGGGTTGTGC3' (located at nucleotide position 3572–3592 in the HPV 45 genome) as the nested reverse primer for 40 cycles. As a control to demonstrate that the assay was able to detect mRNA extracted from HaCaT cells, an additional set of primers specific for cellular-actin was included in the PCR mixture. The forward primer included in the first reaction was 5'GAACCCCAAGGC-CAACCGCGA3' and the reverse primer was 5'CCACACA-GAGTACTTGCGCTCAGG3'. The forward primer included in the nested reaction was 5'GATGACCCAGAT-CATGTTTG3' and the reverse primer was 5'GGAGCAAT-GATCTTGATCTTC3'. All PCR reactions contained 10 mM Tris-HCI, pH 8.3, 50 mM KCl, 2.5 mM MgCl$_2$, 200 M dNTPs, 125 ng of each forward and reverse primer, and 2.5 units of Taq polymerase (PE Biosystems) in a final volume of 50 1. The temperature profile for all reactions was 95 C. for 2 min, followed by 40 cycles of 95 C. for 30 sec., 60 C. for 30 sec, 72 C. for 30 sec, with a final extension at 72 C. for 10 minutes.

All PCR products were separated by electrophoresis on a 2% agarose gel in 1× TBE and visualized by ethidium bromide fluorescence.

EXAMPLE ONE

HPV-18/45 Chimeric VLPs, Lacking the J4 and 195 Epitopes, Elicit Strong Neutralizing Antibody Responses Against Both Viral Types HPV-18 and HPV-45 L1 VLPs were expressed in insect cells using recombinant baculoviruses. The VLPs were purified by CsCl and sucrose gradients and used as coating antigens in an ELISA. Antisera generated in rabbits against a panel of HPV VLP types were tested for reactivity with the HPV-18 and HPV-45 VLPs. As previously reported (White et al., 17th International Papillomavirus Conference), anti-HPV-45 serum strongly cross-reacts with HPV-18 VLPs while antisera to a several other HPV VLP types (-11, -16, -18, -33, -35, -39) display little to no cross reactivity (FIG. 2A). Also, as shown in FIG. 2B, anti-HPV-18 serum reacted most strongly with HPV-45 VLPs as compared to the antisera to the other VLP types. However, the ability of the anti-HPV-18 VLP serum to cross react with the HPV-45 VLPs was less pronounced than the binding of the anti-HPV-45 VLP serum on the HPV-18 VLPs.

Antiserum to HPV-45 has previously been shown (White et al., 17th International Papillomavirus Conference) to neutralize HPV-18 in vitro while antisera to a variety of other HPV types did not inhibit HPV-18 infection (FIG. 3). These results correlate with the binding reactivity of the antisera as seen in FIG. 2A. A titration of the relative neutralizing activity of the two antisera was conducted. As shown in FIG. 4, the anti-HPV-45 serum was 100 fold less potent in its capacity to neutralize HPV-18 than the homotypic antiserum. To test the ability of various anti-HPV VLP sera to neutralize HPV-45, an HPV-45 in vitro infectivity assay was developed which detects a virus-specific transcript (FIG. 5). The results showed that only antiHPV-45 and HPV-18 inhibited HPV-45 in vitro infection. Thus, cross-neutralizing epitopes to both HPV-18 and HPV-45 exist on both of the L1 molecules.

To study type-specific and cross-neutralizing activities against both HPV-18 and HPV45, four different HPV-18/45 chimeric L1 molecules were generated by replacing segments of the HPV-18 molecule with analogous regions of the HPV-45 L I gene. The chimeric L1 molecules were purified from recombinant baculovirus-infected insect cells by CsCl and sucrose gradient centrifugation. Analysis of the different purified chimeric L1 proteins by electron microscopy revealed that all of the novel L1 molecules formed VLPs (data not shown).

The binding of different anti-HPV-18 neutralizing mabs and an anti-HPV-45 to the different HPV-18/45 chimeric VLPs was tested (FIG. 7). Using HPV-18 neutralizing mabs, we have demonstrated that there are a least three neutralizing epitopes on HPV-18 VLPs (R5, J4, and 195). The R5 and J4 epitopes were found to be distinct from one another while the 195 epitope partially overlaps both the R5 and J4 binding sites (Table 2). In this experiment, HPV-18 VLPs were bound to activated CM5 (BIACORE) sensor chips. MAb binding to the immobilized VLPs was measured as an increase in mass (resonance units (RU)). An initial mAb was allowed to bind to the VLPs until a saturating amount was bound. Subsequently, the second mAb was introduced onto the chip. Independent interaction of the two mAbs was indicated by a large increase in the RU. In contrast, a second mAb that bound to a common site as the first mAb was inhibited from binding resulting in little to no increase in RU. For example, when the first and second mAbs were the same antibody, the binding site is identical and further binding by the second antibody was significantly reduced or not detected. This type of experiment, where the first and second antibodies are identical, is shown in columns A, B, and C, where repetitive introduction of mAbs 195, J4, and R5 onto the chip resulted in 0%, 5.5%, and 21% increases respectively. In contrast, in the presence of J4, mAb R5 increased the RU units in a manner similar to when a control antibody was used as the first antibody (column D). Thus, these data indicate that mAbs R5 and J4 bind to distinct sites. The epitope for mAb 195 partially overlaps the epitopes recognized by mAbs R5 and J4.

This is indicated by the partial (54% and 61%, respectively for J4 and R5) inhibition of mAb 195 binding in the presence of either J4 or R5 binding (columns E and F).

TABLE 2

Competitive binding studies with HPV-18 neutralizing mAbs conducted with Biosensor technology

|  | A | B | C | D | E | F |
|---|---|---|---|---|---|---|
| First antibody[a] | 195 | J4 | R5 | J4 | J4 | R5 |
| Second antibody | 195 | J4 | R5 | R5 | 195 | 195 |
| % maximal binding of the second antibody[b] | 0% | 5.5% | 21% | 91.3% | 54% | 61.1% |

[a]The first antibody is introduced onto the VLP-coupled chip until the saturating amount is bound. Then, the second antibody is allowed to bind to the chip.
[b]The percent binding to the second antibody is expressed as a percentage of its total binding (RU) when a control antibody (V5 anti-HPV-16 VLP) was used as the first antibody.

As shown in FIG. 7, the two of the three HPV-18 neutralizing mAbs do not recognize HPV-45 while mAb R5 slightly cross reacts with the heterotypic VLP. Surprisingly, three of the 4 chimeric HPV 18/45 VLPs, including the XN chimeric which exchanges amino acids 53–194, retained binding activity with all three HPV-18 neutralizing mAbs. In contrast, the NB chimeric which exchanges amino acids 267–442, failed to bind J4 and 195 but maintained the R5 binding site.

An HPV-45 neutralizing mAb has not yet been identified. However, the E30 mAb recognizes a conformational epitope (personal communication, Neil Christensen). MAb E30 preferentially recognizes HPV-45 VLPs but binds to HPV-18 VLPs (FIG. 7). The E30 mAb bound to the chimeric VLPs but reacted more strongly with the HPV-45 VLPs.

Groups of Swiss mice (5 mice/group) were immunized with three of the four different chimeric VLPs as well as HPV-18 and HPV-45 VLPs adsorbed to aluminum hydroxide. Pooled serum samples, collected after the secondary immunization, were screened by ELISA for reactivity with HPV-18 and HPV-45 VLPs. As shown in FIG. 8, both the XN and NB chimerics which replace amino acids 53–194 and 267–442 of the HPV-18 L1 with the analogous regions of HPV-45 L1 respectively, elicited antisera that strongly reacted with both HPV-18 and HPV-45 VLPs. In contrast, antisera against the BH chimeric in which C' terminal end (amino acids 449–506) of HPV-18 L1 were replaced with the analogous region of HPV-45 L1, reacted poorly with HPV-45 VLPs. Additionally, there was a predilection of the anti-HPV-18 VLP serum for the homotypic VLP while, the anti-45 antiserum reacted more uniformly with the two parental L1 sequences.

The pooled serum samples from the post-secondary immunization with either HPV-18, HPV-45 or the three chimeric VLPs were tested for neutralizing activity in both the HPV-18 and HPV-45 in vitro infectivity assays (Table 3). HPV-18 and HPV-45 were preincubated with MOUSE serum diluted with serial log10 dilutions of anti-HPV-18 VLP serum, anti-HPV-45 VLP serum, and anti-chimeric VLP serum prior to addition to keratinocytes. HPV-18 and HPV-45 E1 E4-specific and cellular actin-specific RT-PCR products were generated with RNA isolated from the infected cells. The neutralization titer is expressed as the highest serum dilution that inhibited the detection of the virus specific message. The ability of the HPV-45 antiserum to neutralize the heterologous type virus was one log lower than the homologous type virus. The difference is even greater for the anti HPV-18 antisera, which only neutralized HPV45 at 1:100 for the GU1 strain versus a neutralization titer of 1:10,000 on the homologous virus type. The ability of the anti 18/45 serum to neutralize both HPV-18 and HPV-45 is equivalent.

TABLE 3

Neutralization of HPV 18 and HPV 45 by anti-chimeric VLP sera

| Anti-serum | HPV 18 neutralization titer | HPV 45 neutralization titer |
| --- | --- | --- |
| 18 L1GU1 | $10^{-4}$ | $10^{-2}$ |
| 18 L1GU2 | $10^{-4}$ | $<10^{-2}$ |
| 45 L1 | $10^{-3}$ | $10^{-4}$ |
| 18/45 XN | $10^{-2}$ | $10^{-3}$ |
| 18/45 NB | $10^{-4}$ | $10^{-4}$ |
| 18/45 BH | $>10^{-4}$ | $<10^{-2}$ |

The results showed that although the anti-HPV-18 VLP sera neutralized HPV-18 infection at high (1:10,000) dilutions, the neutralizing titer against HPV-45 was below detectable limits. In one experiment and only 1:100 in a second experiment. In contrast, the anti-HPV-45 VLP serum strongly (1:10,000 titer) neutralized the HPV-45 virus and also had significant (1 :1000 titer) neutralizing activity against BPV-18 in vitro infection. The XN 18/45 chimeric L1 VLP elicited relatively low (1:100) HPV-18 neutralization titers as compared to the HPV-18 VLP or the NB and BH chimeric L1 VLPs, each of which induced HPV-18 neutralizing titers of 1:10,000. This results suggest that amino acids 53–194 (XN region) are important for the establishment of HPV-18 neutralizing epitopes or play a role in the proper folding of the epitopes in other regions of the HPV-18 L1 molecule. All three of the HPV-18 neutralizing mAbs (R5, J5, and 195) bound to the XN 18/45 chimeric L1 VLPs. However, the reactivity of the R5 and J4 mAbs against this chimeric VLP appeared to be reduced relative to the level of binding seen on the BH chimeric or the native 18 VLP. Whether the diminution of the binding if these two mAbs to the XN chimeric VLP contributed to the decrease of HPV-18 neutralizing activity or whether some other, currently unidentified, neutralization sites for HPV-18 were lost in the chimeric molecule has not yet been determined. The XN chimeric was, however, also capable of eliciting neutralization titers (1:1,000) against HPV-45.

In contrast to the XN 18/45 chimeric L1 VLPs, the BH chimeric VLPs, reacted strongly with all three HPV-18 neutralizing mAbs. The anti-BH chimeric VLP antiserum strongly (>1:10,000) neutralized HPV-18 in vitro infection but had no detectable activity against HPV-45 infection. Thus, this chimeric VLP, in which only the C' terminus (amino acids 449–506) of HPV-18 L1 were replaced with the analogous sequence of HPV-45 L1, elicited antiserum with similar properties to the intact HPV-18 L1 sequence.

Unexpectedly, the 18/45 chimeric L1 VLP that elicited high-titered antiserum against both HPV-18 and HPV-45 was the NB chimeric VLP. These VLPs, lack both the 195 and the J4 binding sites while retaining the R5 epitope. Screening of the anti-NB chimeric antiserum in both the HPV-18 and HPV-45 neutralization assays showed that the single antiserum neutralized both virus types at serum dilutions as high as 1:10,000. These results again demonstrate the importance of keeping the N' terminus half (amino acids 1–194) of HPV-18 L1 intact for strong anti-HPV-18 neutralizing activity and suggest that either the neutralization epitopes for HPV-45 are in the C' terminus half of the L1 molecule or that the chimeric L1 molecule forms novel neutralizing epitopes capable of neutralizing both viruses.

The results presented above, demonstrate for the first time, that it may be possible to create a single chimeric L1 molecule that induces high-titered neutralizing responses against two or more HPV types. Such a chimeric construct would significantly reduce the cost of producing an HPV vaccine with broad, protective effects against a variety of HPV types. Additionally, the chimeric VLPs may simplify serum screening assays aimed at the detection of antibodies to specific HPV types.

What is claimed is:

1. A chimeric HPV L1 protein comprising HPV-18 L1 protein and HPV-45 L1 protein.

2. The protein of claim 1 wherein said protein includes at least the R5 epitope of HPV-18 L1 protein.

3. The protein of claim 2 wherein said protein includes at least amino acid residues 53 through 194 of HPV-18 L1 protein.

4. The protein of claim 3 wherein said protein includes at least amino acid residues 1–194 of HPV-18 L1 protein.

5. A method of treating papillomavirus caused by at least one of HPV-18 and HPV-45 comprising administering to a patient an effective amount of the protein of claim 1.

* * * * *

SEQUENCE LISTING

<160> NUMBER OF SEQ ID NOS: 26

<210> SEQ ID NO 1
<211> LENGTH: 22
<212> TYPE: DNA
<213> ORGANISM: Artificial
<220> FEATURE:
<223> OTHER INFORMATION: PCR primer

<400> SEQUENCE: 1
gactccaacg acgcagagaa ac                                      22

<210> SEQ ID NO 2
<211> LENGTH: 21
<212> TYPE: DNA
<213> ORGANISM: Artificial
<220> FEATURE:
<223> OTHER INFORMATION: PCR primer

<400> SEQUENCE: 2

-continued

```
gtccacaatg ctgcttctcc g                                              21

<210> SEQ ID NO 3
<211> LENGTH: 22
<212> TYPE: DNA
<213> ORGANISM: Artificial
<220> FEATURE:
<223> OTHER INFORMATION: PCR primer

<400> SEQUENCE: 3
gtatgcatgg acctaaggca ac                                             22

<210> SEQ ID NO 4
<211> LENGTH: 21
<212> TYPE: DNA
<213> ORGANISM: Artificial
<220> FEATURE:
<223> OTHER INFORMATION: PCR primer

<400> SEQUENCE: 4
tccacagtgt ccaggtcgtg t                                              21

<210> SEQ ID NO 5
<211> LENGTH: 34
<212> TYPE: DNA
<213> ORGANISM: Artificial
<220> FEATURE:
<223> OTHER INFORMATION: PCR primer

<400> SEQUENCE: 5
cagatcagat ctatggcttt gtggcggcct agtg                                34

<210> SEQ ID NO 6
<211> LENGTH: 33
<212> TYPE: DNA
<213> ORGANISM: Artificial
<220> FEATURE:
<223> OTHER INFORMATION: PCR primer

<400> SEQUENCE: 6
tatgcaagct tacttcctgg cacgtacacg cac                                 33

<210> SEQ ID NO 7
<211> LENGTH: 33
<212> TYPE: DNA
<213> ORGANISM: Artificial
<220> FEATURE:
<223> OTHER INFORMATION: PCR primer

<400> SEQUENCE: 7
ccatagagat ctatggcttt gtggcggcct agt                                 33

<210> SEQ ID NO 8
<211> LENGTH: 33
<212> TYPE: DNA
<213> ORGANISM: Artificial
<220> FEATURE:
<223> OTHER INFORMATION: PCR primer

<400> SEQUENCE: 8
aagcgaagct tatttcttac tacgtatacg tac                                 33

<210> SEQ ID NO 9
<211> LENGTH: 33
<212> TYPE: DNA
<213> ORGANISM: Artificial
```

```
<220> FEATURE:
<223> OTHER INFORMATION: PCR primer

<400> SEQUENCE: 9
ccatagagat ctatggcttt gtggcggcct agt                            33

<210> SEQ ID NO 10
<211> LENGTH: 30
<212> TYPE: DNA
<213> ORGANISM: Artificial
<220> FEATURE:
<223> OTHER INFORMATION: PCR primer

<400> SEQUENCE: 10
caagaatcta gaactgcctg catgataaaa                                30

<210> SEQ ID NO 11
<211> LENGTH: 30
<212> TYPE: DNA
<213> ORGANISM: Artificial
<220> FEATURE:
<223> OTHER INFORMATION: PCR primer

<400> SEQUENCE: 11
aggcagttct agattattaa ctgtaggcaa                                30

<210> SEQ ID NO 12
<211> LENGTH: 33
<212> TYPE: DNA
<213> ORGANISM: Artificial
<220> FEATURE:
<223> OTHER INFORMATION: PCR primer

<400> SEQUENCE: 12
actaaaatcc atggccccat aacctgtatc cac                            33

<210> SEQ ID NO 13
<211> LENGTH: 28
<212> TYPE: DNA
<213> ORGANISM: Artificial
<220> FEATURE:
<223> OTHER INFORMATION: PCR primer

<400> SEQUENCE: 13
ttggccatgg attttagtac attgcagg                                  28

<210> SEQ ID NO 14
<211> LENGTH: 33
<212> TYPE: DNA
<213> ORGANISM: Artificial
<220> FEATURE:
<223> OTHER INFORMATION: PCR primer

<400> SEQUENCE: 14
aagcgaagct tatttcttac tacgtatacg tac                            33

<210> SEQ ID NO 15
<211> LENGTH: 24
<212> TYPE: DNA
<213> ORGANISM: Artificial
<220> FEATURE:
<223> OTHER INFORMATION: PCR primer

<400> SEQUENCE: 15
gttgtgtatg tgttgtaagt gtga                                      24
```

<210> SEQ ID NO 16
<211> LENGTH: 21
<212> TYPE: DNA
<213> ORGANISM: Artificial
<220> FEATURE:
<223> OTHER INFORMATION: PCR primer

<400> SEQUENCE: 16
gtccacaatg ctgcttctcc g                                    21

<210> SEQ ID NO 17
<211> LENGTH: 21
<212> TYPE: DNA
<213> ORGANISM: Artificial
<220> FEATURE:
<223> OTHER INFORMATION: PCR primer

<400> SEQUENCE: 17
gaattgagct agtagaaagc t                                    21

<210> SEQ ID NO 18
<211> LENGTH: 21
<212> TYPE: DNA
<213> ORGANISM: Artificial
<220> FEATURE:
<223> OTHER INFORMATION: PCR primer

<400> SEQUENCE: 18
tccacagtgt ccaggtcgtg t                                    21

<210> SEQ ID NO 19
<211> LENGTH: 21
<212> TYPE: DNA
<213> ORGANISM: Artificial
<220> FEATURE:
<223> OTHER INFORMATION: PCR primer

<400> SEQUENCE: 19
gagcttacag tagagagctc g                                    21

<210> SEQ ID NO 20
<211> LENGTH: 24
<212> TYPE: DNA
<213> ORGANISM: Artificial
<220> FEATURE:
<223> OTHER INFORMATION: PCR primer

<400> SEQUENCE: 20
tgttaccact acacactttc cttc                                 24

<210> SEQ ID NO 21
<211> LENGTH: 21
<212> TYPE: DNA
<213> ORGANISM: Artificial
<220> FEATURE:
<223> OTHER INFORMATION: PCR primer

<400> SEQUENCE: 21
gcagaggacc ttagaacact a                                    21

<210> SEQ ID NO 22
<211> LENGTH: 21
<212> TYPE: DNA
<213> ORGANISM: Artificial
<220> FEATURE:
<223> OTHER INFORMATION: PCR primer

```
<400> SEQUENCE: 22
gaacacagga gcgggttgtg c                                              21

<210> SEQ ID NO 23
<211> LENGTH: 21
<212> TYPE: DNA
<213> ORGANISM: Artificial
<220> FEATURE:
<223> OTHER INFORMATION: PCR primer

<400> SEQUENCE: 23
gaaccccaag gccaaccgcg a                                              21

<210> SEQ ID NO 24
<211> LENGTH: 24
<212> TYPE: DNA
<213> ORGANISM: Artificial
<220> FEATURE:
<223> OTHER INFORMATION: PCR primer

<400> SEQUENCE: 24
ccacacagag tacttgcgct cagg                                           24

<210> SEQ ID NO 25
<211> LENGTH: 20
<212> TYPE: DNA
<213> ORGANISM: Artificial
<220> FEATURE:
<223> OTHER INFORMATION: PCR primer

<400> SEQUENCE: 25
gatgacccag atcatgtttg                                                20

<210> SEQ ID NO 26
<211> LENGTH: 21
<212> TYPE: DNA
<213> ORGANISM: Artificial
<220> FEATURE:
<223> OTHER INFORMATION: PCR primer

<400> SEQUENCE: 26
ggagcaatga tcttgatctt c                                              21
```